(12) United States Patent
Sigmon, Jr. et al.

(10) Patent No.: US 9,539,090 B2
(45) Date of Patent: Jan. 10, 2017

(54) TRANSAORTIC VALVE ACCESS DEVICE

(71) Applicant: Cook Medical Technologies LLC, Bloomington, IN (US)

(72) Inventors: John C. Sigmon, Jr., Winston-Salem, NC (US); Jillian Haac, Winston-Salem, NC (US); Michelle D. Martinez, Winston-Salem, NC (US); Shaun D. Gittard, Winston-Salem, NC (US); Devesh Amatya, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 367 days.

(21) Appl. No.: 14/156,945

(22) Filed: Jan. 16, 2014

(65) Prior Publication Data
US 2015/0196392 A1 Jul. 16, 2015

(51) Int. Cl.
A61F 2/06 (2013.01)
A61F 2/24 (2006.01)
A61B 17/00 (2006.01)
A61M 25/09 (2006.01)
A61B 17/22 (2006.01)
(Continued)

(52) U.S. Cl.
CPC ........... *A61F 2/2427* (2013.01); *A61B 5/0215* (2013.01); *A61B 17/00234* (2013.01); *A61F 2/2466* (2013.01); *A61M 25/09041* (2013.01); *A61B 5/02158* (2013.01); *A61B 5/6851* (2013.01); *A61B 5/6852* (2013.01); *A61B 2017/00022* (2013.01); *A61B 2017/00243* (2013.01); *A61B 2017/00694* (2013.01); *A61B 2017/22038* (2013.01); *A61B 2017/22098* (2013.01);
(Continued)

(58) Field of Classification Search
CPC ........ A61M 25/09; A61M 25/09041–25/0905; A61M 25/091; A61M 2025/09125; A61M 2025/0001–2025/0003; A61M 25/0113–25/0116; A61B 2017/003–2017/00331; A61B 5/021–5/02158; A61F 2/2427–2/2475
See application file for complete search history.

(56) References Cited

U.S. PATENT DOCUMENTS 4,722,348 A 2/1988 Ligtenberg et al.
5,142,155 A 8/1992 Mauze et al.
(Continued)

FOREIGN PATENT DOCUMENTS

WO WO 01/13789 A1 3/2001

*Primary Examiner* — Victor Nguyen
*Assistant Examiner* — Jonathan Hollm
(74) *Attorney, Agent, or Firm* — Brinks Gilson & Lione

(57) ABSTRACT

A valve insertion device for traversing a wire guide through a valve within an intraluminal passage. A wire guide is positioned near the outflow of a valve within an intraluminal passage. Alongside the wire guide, a pressure sensor is positioned to detect the pressure of the fluid in the intraluminal passage. As the valve opens, the fluid pressure at the outflow of the valve increases. This information is sent from the pressure sensor to a control system. From this information, the control system can determine when the valve will open and can actuate an advancement system to move the wire guide to traverse the open valve. After traversing the valve, various catheters and sheaths may be advanced over the wire guide through the valve.

21 Claims, 3 Drawing Sheets

(51) Int. Cl.
   *A61M 25/00* (2006.01)
   *A61B 5/0215* (2006.01)
   *A61B 5/00* (2006.01)

(52) U.S. Cl.
   CPC ............... *A61B 2090/064* (2016.02); *A61M 2025/0002* (2013.01); *A61M 2025/09116* (2013.01)

(56) References Cited

U.S. PATENT DOCUMENTS

| | | | |
|---|---|---|---|
| 5,752,518 A | 5/1998 | McGee et al. | |
| 6,112,598 A * | 9/2000 | Tenerz | A61B 5/0215 73/756 |
| 6,551,302 B1 | 4/2003 | Rosinko et al. | |
| 9,149,230 B2 * | 10/2015 | Caron | G01F 1/6884 |
| 2004/0097805 A1 | 5/2004 | Verard et al. | |
| 2004/0153135 A1 * | 8/2004 | Haase | A61B 5/026 623/1.11 |
| 2004/0249413 A1 * | 12/2004 | Allen | A61B 17/00491 606/214 |
| 2005/0033343 A1 | 2/2005 | Chermoni | |
| 2006/0146010 A1 * | 7/2006 | Schneider | A61M 25/0105 345/156 |
| 2006/0241465 A1 | 10/2006 | Huennekens et al. | |
| 2006/0287569 A1 | 12/2006 | Schock et al. | |
| 2007/0173861 A1 * | 7/2007 | Strommer | A61B 5/06 606/108 |
| 2008/0221440 A1 | 9/2008 | Iddan et al. | |
| 2009/0036901 A1 * | 2/2009 | Omori | 606/130 |
| 2009/0156960 A1 * | 6/2009 | Mauge | A61M 27/006 600/561 |
| 2009/0177090 A1 | 7/2009 | Grunwald et al. | |
| 2009/0306547 A1 | 12/2009 | Iddan et al. | |
| 2010/0023021 A1 | 1/2010 | Flaherty | |
| 2010/0049062 A1 * | 2/2010 | Ziv | A61B 5/02152 600/486 |
| 2011/0066047 A1 | 3/2011 | Belleville et al. | |
| 2011/0276075 A1 | 11/2011 | Fung et al. | |
| 2012/0041295 A1 | 2/2012 | Schultz | |
| 2012/0220883 A1 | 8/2012 | Manstrom et al. | |
| 2013/0281787 A1 | 10/2013 | Avneri et al. | |

* cited by examiner

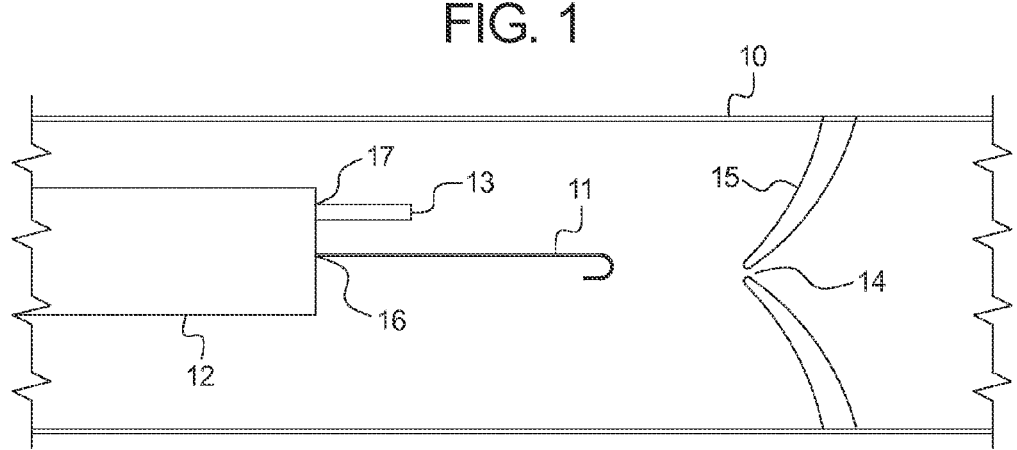
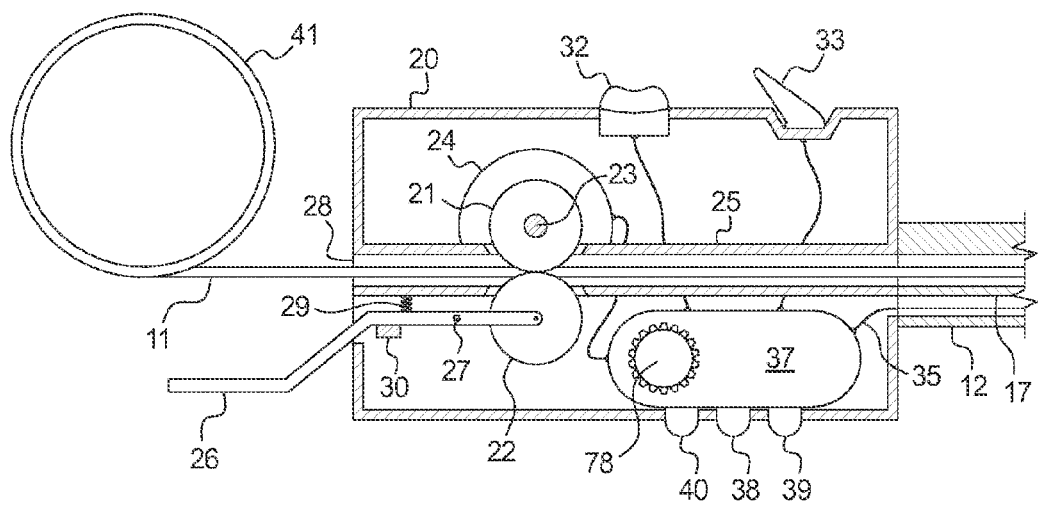

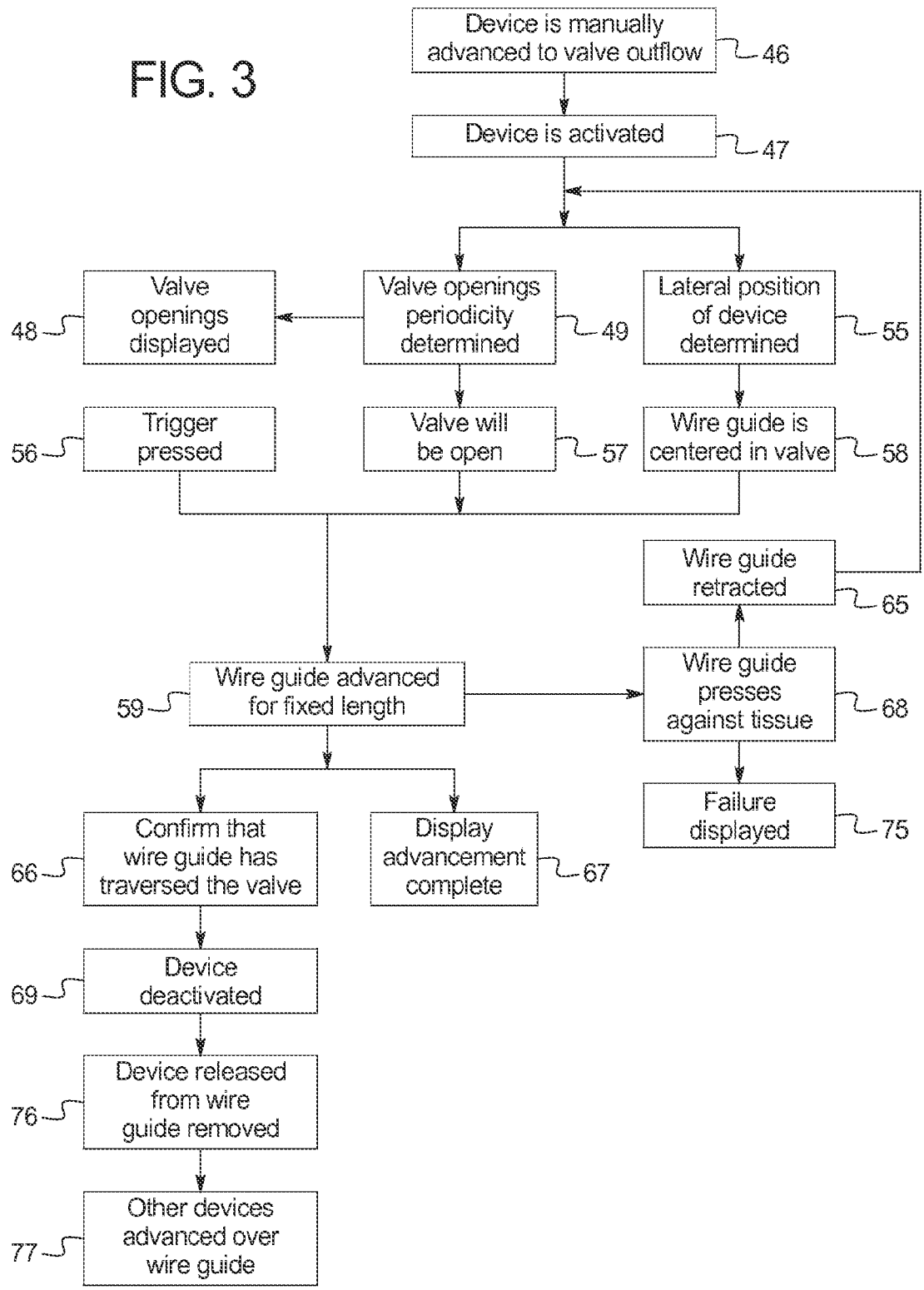

TRANSAORTIC VALVE ACCESS DEVICE

BACKGROUND

The field of the present invention relates to wire guides, catheters, sheaths and other intraluminal medical devices for use in traversing valves within intraluminal passages.

Wire guides are commonly used to pass through narrow passages in the body so that larger catheters and other devices may be advanced through an intraluminal passage along an already established path. Specifically, during valvuloplasty, stenting or left ventricle intervention, a wire guide with a small cross-section is initially advanced through the aortic valve so that larger devices may pass through the valve with less difficulty. However, frequently the leaflets of the aortic valve are stenotic and calcified, making it difficult for surgeons to pass even a wire guide through the valve. Furthermore, the artery leading up to the valve is curved, making it difficult to align a wire guide with the opening of the valve in the center of the artery. If the surgeon misses the opening of the valve, then the guide wire may advance into the coronary sinuses, and may cause damage if too much force is applied. Additionally, fluoroscopy must be used during procedures to assist the surgeon in advancing the wire guide. However, if the wire guide is repeatedly unable to traverse the valve, the patient will be exposed to excessive radiation from a longer procedure.

SUMMARY

A valve insertion device may be used to detect and predict valve openings to more easily traverse a valve with a wire guide. After the wire guide has traversed the valve, larger catheters and devices can traverse the valve over the wire guide. It is also desirable that the automation of traversing the valve will shorten the length of time needed to perform the procedure, and reduce the amount of time a patient must be exposed to radiation.

In view of this, the valve insertion system includes a wire guide or a catheter which is positioned near the outflow of the valve. A pressure sensor is placed alongside the wire guide so that it can detect the fluid pressure of the region near the outflow of the valve. This pressure sensor is connected to a control system which receives information about the pressure at the outflow of the valve.

When the valve opens, it creates a wave of high pressure as fluid 51 escapes from the valve. Using the information gathered by the pressure sensor, the control system can determine when the valve is open. Additionally, by measuring the time between pressure spikes, the control system can predict when the valve will open.

When or just before the control system predicts that the valve will be open, an advancement system is actuated. This advancement system is connected to the wire guide and, when actuated, moves the wire guide through the valve. Once the wire guide has passed through the valve, larger catheters and devices may be advanced over the wire guide through the valve.

BRIEF DESCRIPTION OF SEVERAL VIEWS OF THE DRAWINGS

The invention may be more fully understood by reading the following description in conjunction with the drawings, in which:

FIG. 1 is a side plan view of a valve insertion system within an arterial passage, showing a wire guide, pressure sensors, a catheter, and an aortic valve.

FIG. 2 is a cross-sectional view of a wire guide advancement system.

FIG. 3 is a flow diagram showing the operation of the device.

DETAILED DESCRIPTION

Figure 4:
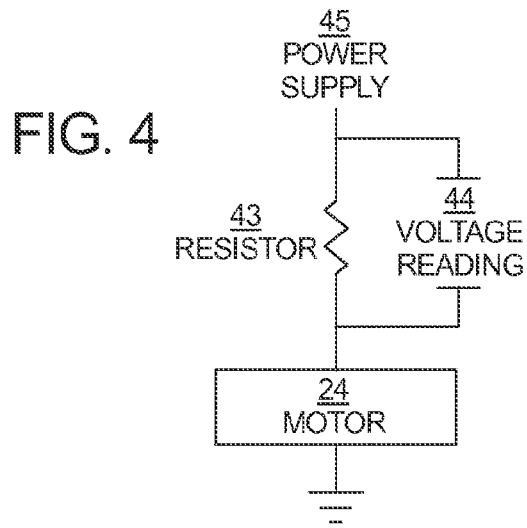
FIG. 4 is an electrical diagram showing a torque transducer.

Referring now to the drawings, and particularly to FIGS. 1 and 2, a wire guide 11 is shown in an intraluminal passage 10 near the outflow of a valve 14. In this embodiment, the wire guide 11 protrudes from a lumen 16 in a catheter 12. The catheter 12 has a pressure sensor 13 within a separate lumen 17 protruding from the catheter 12. Each pressure sensor 13 detects the fluid pressure within a region of the intraluminal passage 10 near the outflow of the valve 14.

The pressure sensors 13 relay pressure information to a control system 37. When the valve leaflets 15 open, a pressure wave is created in the intraluminal passage 10 as fluid 51 escapes from the valve 14. The valve 14 then closes, causing the pressure in the intraluminal passage 10 to drop. From the rise and fall of the pressure, the control system 37 determines when the valve 14 is open and when it is closed. Furthermore, by measuring the time between pressure spikes, the control system 37 can predict when the valve 14 will open in the future.

When or just before the valve 14 opens, the control system 37 automatically actuates an advancement system, as shown in FIG. 2. The advancement system is coupled to the proximal portion of the wire guide 11. When actuated, the advancement system moves the distal portion of the wire guide 11 through the valve 14. After the distal portion of the wire guide 11 has passed through the valve 14, larger catheters and devices may be passed over the wire guide 11 through the valve 14.

Referring to FIG. 2, an advancement system is shown. The proximal portion of the wire guide 11 passes through the housing 20 and is coupled to the advancement system by a clamping mechanism. In the embodiment shown, the clamping mechanism is a pair of wheels 21, 22, but other mechanisms could be used such as geared systems, or frictional pushrods. In the embodiment shown the wire guide 11 is advanced by spinning wheels 21, 22. The drive wheel 21 is rotated by a motor 24 exerting torque through a drive shaft 23, while the free-spinning wheel 22 provides lateral resistance, pressing the wire against the drive wheel 21. Once the control system 37 determines that the valve 14 will be open, it may signal the motor 24 to actuate, which in turn spins the drive wheel 21 and advances the wire guide 11. Throughout the advancement system, the wire guide 11 may be constrained within the housing 20 by guide walls 25 which lead the wire guide 11 to the drive wheel 21.

It may be desirable to preprogram the control system 37 to limit the distance which the advancement system may move the wire guide 11 proximally or distally. If the wire guide 11 is advanced too far after traversing the valve 14, it may move into and inadvertently damage other areas of the body. To prevent this, a desirable range may be predetermined which is long enough for the wire guide 11 to traverse the valve, 14 but short enough to prevent the wire guide 11 from advancing into tissue behind the outflow of the valve 14. Typically this distance will range from 20 mm to 60 mm. Because this distance may vary depending upon the patient, it may be desirable to include a dial 78 on the housing 20 connected to the control system 37, so that the surgeon may adjust the length that the advancement system moves the wire guide 11 when actuated.

After the wire guide 11 has traversed the valve 14, it may be detached from the advancement system. In the embodiment shown, the wire guide 11 is detached by depressing the wire guide release lever 26, which rotates about a pivot 27 and moves the free-spinning wheel 22 away from the wire guide 11 to disengage it from the drive wheel 21. After it has been disengaged, the wire guide 11 may be uncoupled from the advancement system by passing the advancement system over the proximal end of the wire guide 11, or by moving the wire guide 11 laterally through a slot 28 between the guide walls 25, depending on the embodiment. If the wire guide release lever 26 is not depressed, a spring 29 and a block 30 within the housing 20 ensure that the default position of the free-spinning wheel 22 is against the wire guide 11 and the drive wheel 21.

Additionally, in the embodiment shown, the wire guide 11 and pressure sensor 13 are contained within a catheter 12. This catheter 12 is coupled to the housing 20 which ensures that the wire guide 11 can be advanced independently from the catheter 12. Once the wire guide 11 has traversed the valve 14, it may be desirable to retrieve the pressure sensor 13 and catheter 12 so that different catheters and device sheaths may be traversed over the wire guide instead. In this case, the device can be removed by passing the housing 20 and catheter 12 over the proximal end of the wire guide 11.

Furthermore, in the embodiment shown, the control system 37 is contained within the housing 20. The proximal end of the pressure sensor 13 is connected with the control system 37 through an opening 39 on the distal end of the housing 20. The control system 37 receives information from the pressure sensor 13 and can determine when the valve 14 is open. In this embodiment, a light emitting diode (LED) 40 is arranged on the outside of the housing 20 and may act as a display by flashing to indicate when valve 14 is open. The pressure sensor 13 can be disconnected from the control system 37 so that the housing 20 can be used again with a new catheter 12 and pressure sensor 13.

It may be desirable for the device to have a power switch 33 which can be toggled by the operator to activate or deactivate the device. While the device is being positioned near the outflow of the valve 14, for example, it may be preferred to deactivate the device to prevent the control system 37 from causing the wire guide 11 to be advanced. Similarly, once the wire guide 11 has traversed the valve 14, the control system 37 may be deactivated in order to be removed. Furthermore, even if the device is positioned at the outflow of the valve 14, the operator may detect an irregular heartbeat or some other condition which the control system 37 was not designed to overcome. In such a scenario, the operator may wish to deactivate the device to wait for the irregular condition to pass or to attempt to manually traverse the valve 14.

It may also be desirable to have a trigger 32 to activate the control system 37 to allow actuation of the advancement device. If the operator of the device decides to attempt to traverse the valve 14 manually, the information from the pressure sensor 13 may still be valuable to successfully traverse the valve 14. Rather than deactivating the entire device by toggling the power switch 33, the operator may only want to prevent the control system 37 from actuating the advancement system. To facilitate this, the trigger 32, which rests in a first "off" position, prevents the control system 37 from actuating the advancement system unless force has been applied to the trigger 32 to actuate it by moving it to a second "on" position. When the trigger 32 has been actuated and it is in the "on" position, the control system 37 is able to actuate the advancement system when appropriate in response to information from the pressure sensor 13. However, the device may only move the wire guide 11 proximally or distally for one predetermined length while the trigger 32 is held in the "on" position. Further actuations of the advancement system preferably require additional trigger 32 actuations, so that the wire guide 11 is only advanced a single time for each actuation of the trigger 32. Once force is removed from the trigger 32, it will revert back to the "off" position. When the trigger 32 is in the "off" position, the pressure sensor 13 will still send information to the control system 37, and information about the pressure and valve 14 openings can still be displayed for the benefit of the operator. However, when the trigger is in the "off" position, the control system 37 does not advance the wire guide 11 in response to the pressure sensor 13. In the embodiment shown in FIG. 2, the operator can coordinate the manual advancement of the wire guide 11 by watching the flashing of the LED indicator 40. The wire guide 11 may be advanced by depressing the wire guide release lever 26 and manually feeding the wire guide 11 into the intraluminal passage 10 from the spool 41. Alternatively, the wire guide 11 may be manually advanced by the housing 20 while the advancement system engages the wire guide 11.

It may also be desirable to include one or more displays on the housing 20 to aid the operator in using the device. These displays can convey a variety of information and may take the form of indicator lights, analog gauges, or digital numeric panels. In the embodiment shown in FIG. 2, the displays are shown as three indicator LED lights 38, 39, 40, however, more displays may be used. The first display 40 serves the dual purpose of indicating when the device has been powered on and indicating when the valve 14 is open, as detected by the pressure sensor 13. The second display 38, indicates that the wire guide 11 has been advanced by the advancement system after the trigger 32 has been depressed, informing the operator that the device's purpose may be complete. The third display, 39, indicates if the wire guide 11 has pressed against tissue to inform the operator that control system 37 has retracted the wire guide 11 and that the trigger 32 must be depressed again in order repeat the attempt to traverse the valve 14. Alternatively, the success or failure of the wire guide's 11 attempt to traverse the valve 14 could be combined into the third display 39, and the second display 38 could instead be adapted to indicate that the control system 37 is communicating with the advancement system after the trigger 32 has been depressed. As another alternative, if the embodiment of the device is capable of determining the wire guide's 11 lateral position within the intraluminal passage 10, then one of the displays 38, 39, 40 may be adapted to indicate to the operator when the wire guide 11 is centered in the intraluminal passage.

Referring to FIG. 3, a flow diagram is shown detailing operation of an embodiment of the device. Initially, the device is manually advanced to the valve 14 outflow (46) and powered on (47). Once activated, the control system 37 begins receiving information from the pressure sensors 13 in order to determine the periodicity of the valve 14 openings (49) and determine the lateral position of the device within the intraluminal passage 10 (55). The valve 14 openings may be displayed (48). Once the surgeon wants to advance the wire guide 11 through the valve 14, the trigger is pressed (56). While the trigger is pressed (56), the control system 37 will actuate the advancement system and move the wire guide 11 if the valve 14 is open (57), if the wire guide 11 is centered in the intraluminal passage 10 (58). However, not every embodiment of the control system 37 is capable of determining the lateral position of the wire guide 11 within the intraluminal passage 10.

While wire guide 11 is advancing (59) for a fixed length, the wire guide 11 will either traverse the valve 14 or press against the tissue near the valve 14. If the wire guide 11 presses against tissue, a torque transducer will indicate to the control system 37 that the wire guide 11 has been pressed against tissue (68). If the advancement system advances the wire guide 11 for a fixed length without retracting, an indicator light 38 on the housing 20 can display this to the operator (67). The operator can then confirm that the wire guide 11 has actually traversed the valve 14 through a method such as radioscopy (66). The device can then be powered off (69), released from the wire guide 11, and removed from the intraluminal passage 10 (76) over the proximal end of the wire guide 11. After removal, larger sheaths and catheters can be advanced to the valve 14 over the wire guide 11 (77). If, however, the wire guide 11 fails to traverse the valve 14 and instead presses against tissue (68), this status can be displayed on an indicator 39 as well (75). After the control system 37 detects that the wire guide 11 is pressing against tissue, it will signal the advancement system to retract the wire guide 11 for whatever distance the wire guide 11 has advanced (65). The trigger may then be released and pressed again (56) to reactivate the control system 37 will then repeat the advancement attempt if desired.

Referring to FIG. 4, an electrical diagram is shown for a torque transducer. The torque transducer measures the voltage 44 across the motor 24 of the advancement system. Because current and voltage within a circuit are directly proportional and determinable where a constant resistance 43 is present, the voltage measurement 44 can also be used to determine the amount of current passing through the circuit. This information is sent to the control system 37, which can determine whether the distal end of the wire guide 11 is pressing against tissue. If the wire guide 11 misses the opening of the valve 14 and instead presses against the tissue of the intraluminal passage 10, the current passing through the motor 24 will increase. When the control system 37 detects a spike in current, it can send a signal to the motor 24 to retract the wire guide 11. Once the wire guide 11 is back at the outflow of the valve 14, the process of sensing valve openings and advancing the wire guide 11 through the valve 14 can be repeated.

Figure 5:
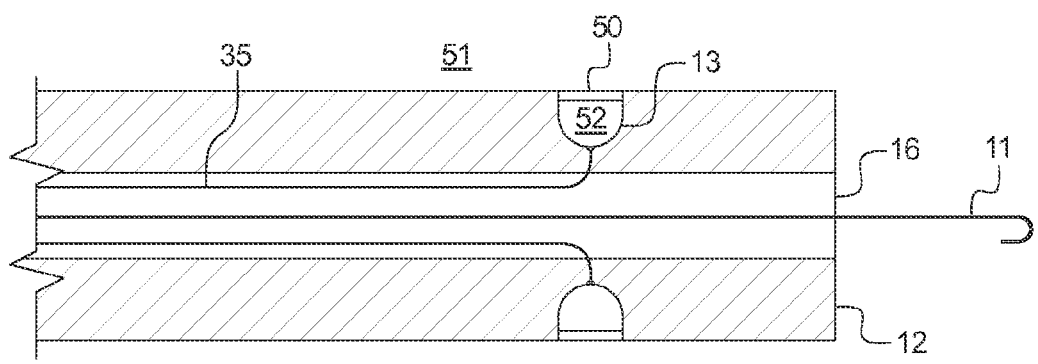
FIG. 5 is a cross-sectional plan view of a valve insertion device showing a wire guide, a catheter, and a pressure sensor built into the walls of the catheter.

Referring to FIG. 5, a catheter 12 is shown with pressure sensors 13, and a wire guide 11. In the embodiment shown, a wire guide 11 is positioned near the valve 14 within a lumen 16 at the center of a catheter 12 having at least two pressure sensors 13. In this particular embodiment, the pressure sensors 13 are positioned on openings along the outer surface of catheter's 12 distal end. Other embodiments could, however, place the pressure sensors within additional lumens in the catheter forming openings on the distal tip of the catheter. Optimally, the pressure sensors 13 should be placed as far apart from each other as possible, such as on opposite sides of the catheter 12.

The pressure sensors 13 may include a surface strain gage 50 with one side exposed to the fluid 51 of the intraluminal passage 10. The other side of the strain gage 50 may be exposed to an ambient fluid 52 of a known pressure. As the strain gage 50 deforms according to the difference in pressure between the two fluids, the resistance changes in a Wheatstone bridge. The corresponding difference in voltage can be transmitted to the control system 37 through a signal wire 35 to determine the pressure of the fluid 51 within the intraluminal passage 10. The signal wire 35 may be connected to the control system 37 through a lumen 16 in the catheter shared by the wire guide 11, or within a separate lumen 17 in the catheter.

While the catheter 12 is positioned near the valve 14, the pressure sensors 13 will transmit information to the control system 37 about the fluid pressure at different areas within the cross-section of the intraluminal passage 10. Due to the shape of the valve leaflets 15 and the way in which the valve 14 opens, a pressure wave is created when the valve opens in which the highest pressure is located in the center of the cross-section of the intraluminal passage 10. The pressure in the passage generally decreases laterally in proportion to the distance from the center of the passage 10. As a result of this relationship, laterally-spaced pressure sensors 13 may be used in some embodiments to determine the catheter's 12 lateral position in the intraluminal passage 10. If one pressure sensor 13 registers a significantly higher pressure than another sensor, then the part of the catheter 12 where the high pressure is located is closest to the center of the intraluminal passage 10. Once all the pressure sensors 13 read approximately similar pressures, the control system 37 can determine that the catheter 12 is centered within the passage 10 and actuate the motor 24 to advance the wire guide 11 through the valve 14.

Additionally, because patients in such surgeries are likely to be under fluoroscopy during a procedure using this device, it may be useful to include radiopaque markers on a catheter 12 near the pressure sensors 13, so that the operator can ensure accurate pressure readings by viewing the location of the pressure sensors 13 relative to the valve 14. Although wire guides are typically made of radiopaque materials such as stainless steel or nitinol, if the wire guide 11 is made of some other material which is not visible under radiation, it may be desirable to place a radiopaque band around the wire guide 11 to observe the wire guide's 11 position before and after traversing the valve 14.

Figure 6:
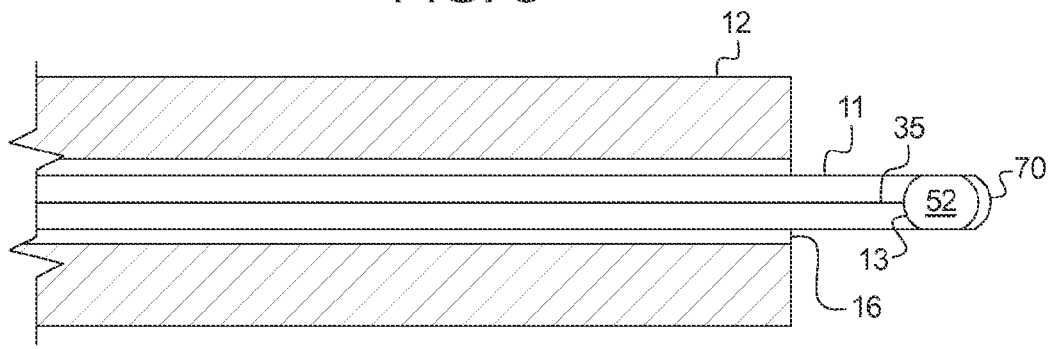
FIG. 6 is a cross-sectional view of a valve insertion device showing a wire guide, a catheter, and a pressure sensor.

Referring to FIG. 6, a catheter 12, wire guide 11, and pressure sensor 13 are shown. In the embodiment shown, the pressure sensor 13 is contained within the wire guide 11, with the strain gage 50 comprising the tip of the wire guide 11. In this embodiment the ambient fluid 52 may be contained in the area immediately behind the strain gage 50. A signal wire 35 conveys pressure information to the control system 37. The strain gage 50 may be curved to make the tip of the wire guide 11 atraumatic to prevent the wire guide 11 from damaging tissue while positioning it near the valve 14 or while traversing the valve 14.

In the embodiment shown, the pressure sensor 13 would be able to detect when the wire guide 11 was pressing against tissue, as the solid tissue would deform the strain gage 50 substantially more than the fluid 51 in the intraluminal passage 10. Therefore, when the pressure sensor 13 indicates a spike in pressure beyond a certain threshold, it would signal that the wire guide 11 has pressed against tissue. In response, the control system 37 could signal the advancement system to retract the wire guide 11 and repeat the process.

Throughout this description, when using the term "wire guide", it is to be understood that this term encompasses a number of elongate medical devices, including at least wires, catheters, and sheaths.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:

1. A valve insertion device comprising,
a wire guide having proximal and distal portions;
a pressure sensor positioned near the distal portion of the wire guide, wherein the pressure sensor detects fluid pressure information of an area within an intraluminal passage near a valve;
an advancement system coupled to the wire guide wherein the advancement system is configured to move the distal portion of the wire guide through the valve; and
a control system configured to receive the fluid pressure information from the pressure sensor to determine when the valve is open, and actuate the advancement system to move the distal portion of the wire guide through the valve when the valve is open.

2. The valve insertion device of claim 1, further comprising a torque sensor which is capable of measuring electrical current being delivered to the advancement system, wherein a large increase in electrical current signals the control system to retract the wire guide.

3. The valve insertion device of claim 2, further comprising a trigger having a first position and a second position, wherein the advancement system may be actuated by the control system when the trigger is in the second position, and wherein the advancement system, when actuated by the control system, proximally or distally moves the distal portion of the wire guide a predetermined distance.

4. The valve insertion device of claim 3, further comprising a power switch capable of activating and deactivating the control system, and a display indicating information received from the control system regarding when the valve is open.

5. The valve insertion device of claim 4, wherein there are a plurality of pressure sensors, and wherein the control system can determine a lateral position of the wire guide in the intraluminal passage by comparing the information received by each pressure sensor.

6. The valve insertion device of claim 1, wherein there are a plurality of pressure sensors, and wherein the control system can determine a lateral position of the wire guide in the intraluminal passage by comparing the information received by each pressure sensor.

7. The valve insertion device of claim 1, wherein the advancement system, when actuated by the control system, proximally or distally moves the distal portion of the wire guide a predetermined distance.

8. The valve insertion device of claim 1, further comprising a power switch capable of activating and deactivating the device.

9. The valve insertion device of claim 1, further comprising a trigger having a first position and a second position, wherein the advancement system may be actuated by the control system when the trigger is in the second position.

10. The valve insertion device of claim 9, wherein the pressure sensor is contained within a lumen in a catheter and wherein the pressure sensor has a distal end positioned on an opening along an outer surface of a distal end catheter.

11. The valve insertion device of claim 1, further comprising a display indicating information received from the control system regarding when the valve is open.

12. The valve insertion device of claim 1, wherein the pressure sensor is built into the wire guide.

13. The valve insertion device of claim 1, wherein the wire guide is detachably coupled to the advancement system through a clamping mechanism.

14. The valve insertion device of claim 1, further comprising a housing containing the advancement system and the control system, wherein the wire guide passes through the housing.

15. The valve insertion device of claim 14, wherein the housing may be separated from the wire guide by passing a proximal end of the wire guide through the housing.

16. A method of passing a device through a valve, comprising,
positioning an elongate medical device having a distal portion within an intraluminal passage near a valve;
positioning a pressure sensor alongside the distal portion of the elongate medical device;
detecting fluid pressure information within the intraluminal passage near the valve after an opening of the valve;
sending fluid pressure information from the pressure sensor to a control system;
predicting by the control system when the valve will be open using the fluid pressure information from a plurality of the openings of the valve; and
actuating an advancement system coupled to the elongate medical device such that the elongate medical device moves through the open valve, wherein the actuation is automatically caused by the control system.

17. The method of claim 16, further comprising:
detecting when the elongate medical device is pressing against tissue by registering a signal in the control system from a torque sensor; and
retracting the elongate medical device by actuating the advancement system.

18. The method of claim 16, further comprising:
detecting when the elongate medical device is pressing against tissue by registering a signal in the control system from a pressure sensor contained in the distal portion of the elongate medical device; and
retracting the elongate medical device by actuating the advancement system.

19. The method of claim 16, wherein a plurality of pressure sensors are contained within a plurality of lumens within a catheter and wherein the control system can determine a lateral position of the elongate medical device in the intraluminal passage by comparing the information received by each pressure sensor.

20. The method of claim 16, further comprising:
uncoupling the advancement system from the elongate medical device after the elongate medical device has traversed the valve; and
retracting the pressure sensor from the intraluminal passage without substantially moving the position of the elongate medical device.

21. The method of claim 16, wherein the elongate medical device is positioned on a downstream side of the valve.

* * * * *